US008548772B2

(12) United States Patent
Brouwer et al.

(10) Patent No.: US 8,548,772 B2
(45) Date of Patent: Oct. 1, 2013

(54) AUTOMATED METHOD AND APPARATUS FOR DETECTING ERRONEOUS SAMPLE COLLECTION IN CLINICAL ASSAYS

(75) Inventors: Eric Brouwer, Ottawa (CA); Jody Ann Tirinato, Plainsboro, NJ (US); Michael P. Zelin, Plainsboro, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 0 days.

(21) Appl. No.: 13/565,930

(22) Filed: Aug. 3, 2012

(65) Prior Publication Data

US 2012/0295359 A1 Nov. 22, 2012

Related U.S. Application Data

(63) Continuation of application No. 12/339,886, filed on Dec. 19, 2008, now Pat. No. 8,265,904.

(60) Provisional application No. 61/015,582, filed on Dec. 20, 2007.

(51) Int. Cl.
*G06F 11/07* (2006.01)
*G06F 11/00* (2006.01)
*G01N 33/20* (2006.01)
*G01N 33/49* (2006.01)

(52) U.S. Cl.
USPC .............. 702/185; 702/183; 436/50; 436/74; 436/79; 436/176; 205/779; 205/789.5

(58) Field of Classification Search
None
See application file for complete search history.

(56) References Cited

U.S. PATENT DOCUMENTS

| 4,680,177 | A | 7/1987 | Gray et al. |
| 5,096,669 | A | 3/1992 | Lauks et al. |
| 5,112,455 | A | 5/1992 | Cozzette et al. |
| 5,200,051 | A | 4/1993 | Cozzette et al. |
| 5,212,050 | A | 5/1993 | Mier et al. |
| 5,447,440 | A | 9/1995 | Davis et al. |
| 5,628,961 | A | 5/1997 | Davis et al. |
| 2006/0060471 | A1 | 3/2006 | Murphy et al. |
| 2007/0066928 | A1 | 3/2007 | Lannoy |

OTHER PUBLICATIONS

International Preliminary Report on Patentability for PCT/US2008/087813 mailed Sep. 7, 2012.
i-STAT System Manual (2004) Abbott Point of Care, East Windsor, NJ, Revised Jul. 12, 2004.
Tate, et al., "Interferences in Immunoassay," Clin. Biochem. Rev. 2004, 25, pp. 105-120.
Fermann, "Point of care testing in the emergency department," The Journal of Emergency Medicine 2002, 22, pp. 393-404.
Shek, "Errors due to heparin in the estimation of plasma sodium and potassium concentrations," Intensive Care Medicine 1985, 11, pp. 309-311.
International Search Report and Written Opinion for PCT/US2008/087813 mailed Mar. 19, 2009.

*Primary Examiner* — Yelena G Gakh
*Assistant Examiner* — Michelle Adams

(57) ABSTRACT

An automatic method for identifying biological samples that are collected using the wrong blood preservative for subsequent analytical testing. The method also provides for identification and/or suppression of certain analytical test results that are substantially or partly adversely affected. The invention is particularly suited for use in point-of-care medical diagnostic testing.

11 Claims, 3 Drawing Sheets

AUTOMATED METHOD AND APPARATUS FOR DETECTING ERRONEOUS SAMPLE COLLECTION IN CLINICAL ASSAYS

CROSS-REFERENCE TO RELATED APPLICATIONS

This application is a continuation of U.S. application Ser. No. 12/339,886 filed on Dec. 19, 2008, which claims priority to Provisional U.S. Patent Application No. 61/015,582, filed on Dec. 20, 2007, the entire contents of which are incorporated herein by reference.

FIELD OF THE INVENTION

The invention relates generally to an apparatus/method for sample collection in clinical assays, and more particularly to an apparatus/method for preventing and detecting erroneous sample collection.

BACKGROUND OF THE INVENTION

In the clinical chemistry laboratory art, it is well known that certain blood tests and assays require certain preservatives to be used if those tests are to be performed reliably. The main reason is that blood tends to coagulate rather quickly and certain blood test reagents require that the blood sample be in a fluid state to permit mixing. Another reason is that the fluidic systems on which several blood analyzers are built require that the blood remains in a fluid state so that blockages of conduits and chambers are avoided and the sample can be effectively washed from the testing chamber after the test is complete. Several anticoagulation reagents are available and these inhibit in various well known ways, the natural coagulation process. For example, calcium ions are required as part of the coagulation cascade, so by adding excess ethylenediaminetetra acetic acid (EDTA) to the blood sample at the time of collection, the calcium ions can be sequestered, by coordination with the EDTA, and coagulation prevented. As is well known in the clinical chemistry art, only certain anticoagulants are suitable for certain blood tests.

From a clinical perspective, when a user (e.g. nurse, physician, phlebotomist), decides a certain blood test or set of blood tests is required, the user then selects the appropriate collection device. This is typically a coated capillary tube, if the sample is to be taken using a fingerstick, e.g. by means of a lancet. More typically, venipunture is used, where a needle is inserted into a vein and the other end of the needle is mated with an evacuated collection tube. This is generally done using a Vacutainer® which is an evacuated tube with a colored stopper. The evacuated tube also contains a blood sample stabilizing reagent or preservative, which can be a heparin salt, a chelating agent such as EDTA, or some other anticoagulant material. The color of the stopper is generally used as a simple means to identify the anticoagulant reagent in the tube, e.g. green stopper for heparin, purple for EDTA, and so on. While users are generally experienced in selecting the correct tube for a given test set, there is still the opportunity for error in tube selection. This is because the user, typically a nurse, is busy and has many other tasks to complete and can be interrupted during any given task. For background on Vacutainer® see: http://en.wikipedia.org/wiki/Vacutainer. Some facilities actually restrict themselves to one collection tube manufacturer in the interest of eliminating errors.

A widely used indirect strategy in the laboratory testing art that can catch such errors in collection tube selection, is to place a reportable range on a given blood test, and if an individual sample analysis is outside of the reportable range, then an algorithm within the analyzer flags or otherwise identifies the test result as unreportable or out of range. However, there are many reasons why an analysis system may flag a given test result as being unreportable that are not based on incorrect sample collection. These include the possibility that the sensor or detection means is not operating to specification due, for example, to one or more of the following; an incomplete wash cycle, temperature fluctuation outside a preset range, calibration malfunction and expired reagent. Those skilled in the art that will recognize that these are but a few of the potential reasons. Among them of course is the possibility that the sample was collected using the wrong anticoagulant. However, prior art systems do not provide a means for isolating the latter reason as the specific cause and explicitly identifying this cause to the user.

By way of confirmation of the state of the art, in experiments showing that when an EDTA sample was intentionally run on prior art electrolyte analyzing instruments, e.g. i-STAT® and a radiometer, only the potassium and calcium results are suppressed, as would be expected as these values should be out of range. None of the other tests provided by the prior art instruments, e.g. $pO_2$, pH, $pCO_2$ and lactate were flagged as being abnormal and there was no indication by the instrument that the wrong type of collection device had been used.

Because the answer from these analyzers are often used to make a clinical decision that can significantly impact the health and well-being of a patient, there remains a need for blood analysis systems to integrate an ability to distinguish the specific cause of a failed blood analysis, notably where the cause is the use of an incorrect sample collection method. Furthermore, subtle effects that are less pronounced on sensor performance and are not typically recognized as being caused by incorrect anticoagulation, need to be identified. The present invention seeks to ameliorate these deficiencies in the prior art and also provide automatic means for alerting users to incorrect sample collection for given test sets.

SUMMARY OF THE INVENTION

The present invention is intended to provide an improved means for detecting and preventing hospital error in the analysis of a blood sample when the sample is collected in a collection tube, which is unsuitable for the intended blood analysis. The disclosed method provides a simple and useful means for ensuring that results obtained from incorrect types of collection tubes are not reported as clinically valid results. In addition the present invention provides a means for alerting the user to the specific cause, where that cause is collection of the sample in the wrong collection device. The user may then be instructed by means of the present invention, when embodied into an analytical system, as to the correct sampling device or method. The analysis cycle may then be repeated using this device or method.

While the present invention is useful for laboratory-based clinical chemistry testing, it is particularly useful for point-of-care, bedside testing, emergency room, physician's office, clinic, blood bank, operating room, laboratory or nursing home testing, remote testing, e.g. a cruise ship or MASH unit, and mobile testing, e.g., in an ambulance. It is particularly useful when embodied in an analytical system where collection of the sample and performance of the test or assay, occur at the same location, as in point-of-care testing (also termed near-patient testing and bedside testing). However, it is understood that in addition to clinical testing laboratory, the invention may be used in any laboratory, including but not limited to research or governmental.

The present invention specifically relates to automatically identifying the presence of the wrong blood preservative in the collection tube, by means of recording the value of certain tests with an analysis system and providing an algorithm to identify the erroneous sample collection device. This is done by analyzing the output signatures of various detection means, e.g. sensors, used to perform the tests. By using the algorithm, erroneous results can be flagged, whereas tests run using the correct preservative will be passed. Where a combination of tests is run on a sample using the analysis system, and where only some of these tests are adversely affected by a certain preservative, then the algorithm is capable of flagging only those tests that are affected and displaying good results for the others. Optionally, the analyzer displays a message reminding the user of the correct type of collection device or anticoagulant.

It is an object of the invention to provide an automatic method for determining that a collection device with an anticoagulant was incorrectly used to collect a blood sample for analysis of analyte species in a sample where the correct collection device for the sample omits a selected anticoagulant; the method comprising; (a) adding a sample from a collection device to an analyzer instrument having means for analyzing species that include a monovalent ion and divalent cation and at least one other analyte, (b) determining the concentration of monovalent ion, divalent cation and one or more other analyte in said sample, (c) comparing the monovalent ion concentration to a predetermined upper threshold value and the divalent cation concentration to a predetermined lower threshold value, and where both said threshold concentration values are surpassed said analyzer instrument reports that concentration values for the monovalent ion, divalent cation and one or more of the other analyte species in said sample should not be used, and (d) said analyzer reports that the sample was collected with the wrong anticoagulant.

It is a further object of the invention to provide an automatic method for determining that a collection device with an anticoagulant was incorrectly used to collect a blood sample for analysis of analyte species in a sample where the correct collection device for the sample omits a selected anticoagulant; the method comprising; (a) adding a sample from a collection device to an analyzer instrument having means for analyzing species that include a divalent cation and at least one other analyte, (b) determining the concentration of a divalent cation and one or more other analyte in said sample, (c) comparing the divalent cation concentration to a predetermined lower threshold value, and where said threshold concentration value is surpassed said analyzer instrument reports that concentration values for the divalent cation and one or more of the other analyte species in said sample should not be used, and (d) said analyzer reports that the sample was collected with the wrong anticoagulant.

It is a further object of the invention to provide a method of identifying the erroneous collection of a blood sample for the measurement of one or more ionic species in a collection device containing a cationic salt of a calcium binding agent comprising: taking a blood sample from a collection device and determining the cation concentration in the sample with respect to an upper threshold value and determining the calcium ion concentration in the sample with respect to a lower threshold value, flagging or suppressing the reporting of the cation, calcium and at least one other measured ionic species in said blood sample when both the cation concentration is above the upper threshold and the calcium concentration is below the lower threshold, and reporting that the type of collection device is inappropriate for collection of a blood sample for the measurement of one or more other selected ionic species.

It is a further object of the invention to provide a method of identifying erroneous collection of a biological sample for the measurement of a first species, in a collection device containing a reagent incompatible with the reliable measurement of said first species comprising; taking a sample from a collection device and determining the concentration of a second species in the sample with respect to a threshold value, flagging or suppressing the reporting of a measured concentration of said first and second species where the concentration of the second species is beyond said threshold value and reporting that the type of collection device is suspected of being inappropriate for collection of a sample for the measurement of said first and second species.

It is a further object of the invention to provide a method of identifying erroneous collection of a biological sample for the measurement of at least one species, in a collection device containing a reagent incompatible with the reliable measurement of said at least one species comprising; taking a sample from a collection device and determining the concentration of a plurality of other species in the sample with respect to a threshold value for each of said species, flagging or suppressing the reporting of a measured concentration of said plurality of species and the at least one species where the concentration of each of said plurality of species is beyond said threshold value and reporting that the type of collection device is suspected of being inappropriate for collection of a sample for the measurement of said at least one species and said plurality of species.

It is a further object of the invention to provide an automatic method for determining that a collection device was incorrectly used to collect a blood sample for analysis of ionic species; the method comprising, adding a sample from a collection device to an analyzer instrument having means for analyzing ionic species that includes a divalent cation, determining the concentration of the divalent cation and one or more other ionic species in said sample, comparing the divalent cation concentration to a predetermined threshold value, and where said threshold concentration value is surpassed said analyzer instrument reports that concentration values for the divalent cation and one or more other ionic species in said sample should not be used and reports that the sample was collected with the wrong anticoagulant.

It is a further object of the invention to provide an automatic analyte testing method for distinguishing blood samples incorrectly collected with the wrong anticoagulant from samples collected using the correct anticoagulant comprising the steps; (a) introducing a collected sample into an analyzer instrument having means for determining the concentration of at least two analytes in a sample, (b) determining the concentration of a first analyte and one or more other analyte in said sample, (c) comparing the first analyte concentration to a predetermined threshold value, (d) where said threshold concentration value is not surpassed said analyzer instrument reports that concentration values for the first analyte and one or more other analytes in said sample, and (e) where said threshold concentration value is surpassed said analyzer instrument reports that concentration values for the first analyte and one or more other analytes in said sample should not be used, and reports that the sample was collected with the wrong anticoagulant.

The present method is particularly advantageous where sensors for divalent cations, notably calcium and magnesium are used to identify inappropriate anticoagulation protocols. For example, a sensor output is coupled to an analysis algorithm where the divalent cation sensor is for calcium and the algorithm sets a concentration threshold of below about 0.25 mM. Here, the analysis system tests for several other ionic species including magnesium, chloride, bicarbonate, potassium, sodium, lithium, ammonium and hydrogen ions.

The method is particularly advantageous for identifying EDTA collection devices where the device is a tube contain EDTA with a stopper sealing the entry to the tube and where the interior of the tube is under a partial vacuum. In addition it can be used to identify other collection devices containing EDTA including a test tube, a syringe and a capillary tube, whether it be made polyethylene terephthalate (PET), polypropylene, polyolefin, polyethylenenapthalate polyvinyl chloride, glass, or other materials.

The method is appropriate for analyzer instruments comprising a laboratory analyzer with one or more reusable sensors, and also where the analyzer instrument comprises an analyzer used in combination with one or more single-use test cartridges. Furthermore, these single-use test cartridges may have one or more sensors.

Where determination of the divalent cation concentration is by a sensor, an ion-selective electrode, optode, flame photometer, ion-sensitive dye and divalent cation-dependent enzyme assay can all be used. Other detection means will be apparent to those skilled in the art of analytical chemistry and analytical biochemistry. However, the method is typically conceived to use electrochemical detection means, e.g. a calcium ion-selective electrode, or optionally, a magnesium ion-selective electrode.

Where determination of the ion concentration of other species is by a sensor, an ion-selective electrode, optode, flame photometer, ion-sensitive dye and divalent cation-dependent enzyme assay can all be used. Other detection means will be apparent to those skilled in the art of analytical chemistry and analytical biochemistry. The method is typically conceived to use electrochemical detection with an ion-selective electrode to measure these other ions including calcium, magnesium, chloride, bicarbonate, potassium, sodium, lithium, ammonium and hydrogen.

Where the method incorporates a reporting step, this is generally by means of a display screen on an analyzer instrument or an audio alert or message, and the analyzer will generally be placed at a point-of-care location, e.g. an emergency department, operating room, physician's office and ambulance.

Typically, the sample type contemplated for the disclosed method is whole undiluted blood, but it can also be plasma, serum and diluted and amended samples of all these.

Where the method incorporates the use of threshold values, calcium thresholds are generally selected to be a value in the range of about 0.001 mM to about 0.3 mM, and potassium threshold values are generally in the range of about 8 mM to about 20 mM. In methods where a sodium threshold is used, this is generally at or above about 160 mM.

Those skilled in the art will recognize that suppressing or flagging a measured value of an analyte, e.g. an ionic species, based on it alone exceeding a threshold value is widely used. However, the present methods disclose means for systematically identifying other measured species, that alone do not necessarily exceed a threshold, but which should be suppressed or flagged. In addition, the present method provides automatic means for identifying blood samples that were collected with the wrong anticoagulation protocol, for a given test or set of tests, and identifying that cause to the user.

It will be appreciated by those skilled in the art, while the disclosed methods generally focus on identification of erroneous collection of samples with EDTA, they are also applicable with appropriate modification to sample collection with any art-disclosed anticoagulant agent such as, but not limited to, salts of EDTA such as $K_2$EDTA, $K_3$EDTA, and $Na_2$EDTA, ethylene glycol tetra acetic acid (EGTA) and its salts, oxalic acid and its salts such as potassium oxalate, citric acid and its salts such as trisodium citrate, fluorides such as sodium fluoride, non-balanced heparins such as sodium heparin, and combinations thereof. Additional anticoagulants should be known to one of skill in the art. As a result, the present methods provide a useful advance in the clinical chemistry arts for providing quality results on patient samples.

Other features and advantages of the invention will become apparent from the following detailed description, taken in conjunction with the accompanying figures, which illuminate, by way of example, various features of embodiments of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

Figure 1:
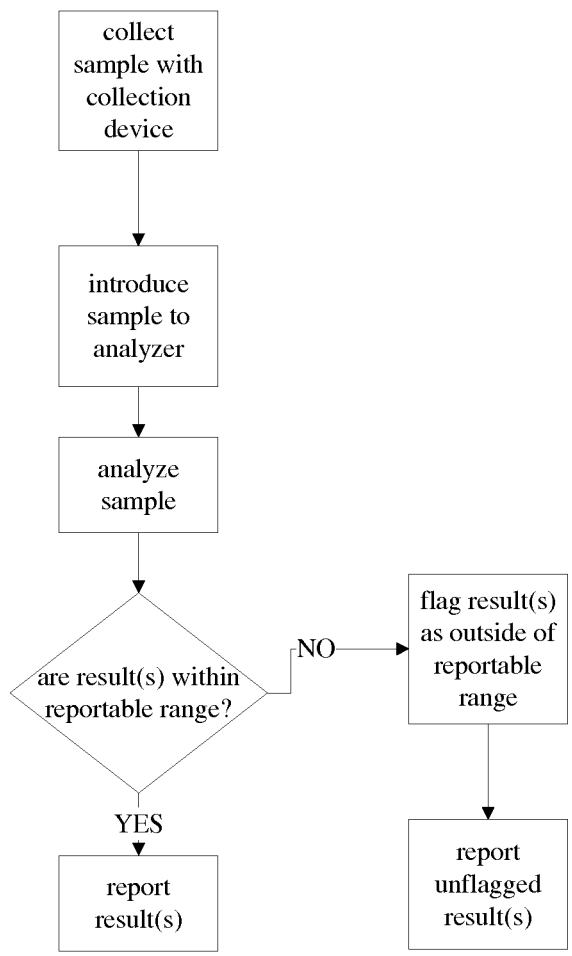
FIG. 1 is a flow chart illustrating the prior art algorithm for flagging erroneous test results.

A system and method for preventing and detecting erroneous sample collections are disclosed. The system and method are based on the i-STAT® point-of-care blood testing system which uses disposable cartridges with sensors for performing one or more blood test. These cartridges are operated using a portable analyzer which has a display for providing test results and other information to the user. The i-STAT® system is described in detail by the i-STAT® System Manual (2007) (Abbott Point of Care, East Windsor, N.J.), which is incorporated here in its entirety. One skilled in the art will recognize that the disclosed methods can be adapted to other blood testing systems, both those used at the point-of-care and in a central laboratory. It is also understood that the disclosed methods can be adopted to other handheld analyzers or combination testing cartridges and portable clinical analyzers, including, but not limited to, those having advanced bioscience technology, and including those which are available or may become available.

In an exemplary embodiment, point of care blood analysis systems are generally based on a re-usable reading apparatus that performs blood tests such as, but not limited to, electrolytes, blood gases, chemistries, coagulation, hematology, glucose and cardiac markers. Point of care blood analysis systems perform blood tests using a disposable cartridge that contains (i) analytical elements, such as microfabricated biosensors, e.g. electrodes for sensing analytes such as pH, oxygen and glucose; (ii) fluidic elements, e.g. conduits for receiving and delivering the blood sample to the electrodes; and (iii) calibration elements, e.g. aqueous fluids for standardizing the electrodes with a known concentration of each analyte. The reading apparatus contains the electronics and algorithms for operating the electrodes, e.g. making the measurements and doing computations. The apparatus also has the ability to display results and communicate those results to the laboratory and hospital information systems (LIS, HIS), optionally via a computer workstation. Communication between the reader and a workstation is via various means including an infrared link, and between the workstation and a laboratory information system via a hard wire connection or other similar means. Those skilled in the electronics and communications arts will recognize that optionally, other data transmission means can be used, e.g. various wireless protocols.

Several technologies within the general areas of sensing electrodes, measurement methods, single-use cartridges and readers (also referred to as analyzers and instruments) are disclosed in jointly owned i-STAT® patents and incorporated by reference here: U.S. Pat. No. 5,112,455; U.S. Pat. No. 5,096,669; U.S. Pat. No. 5,212,050; U.S. Pat. No. 5,200,051 and U.S. Pat. No. 5,447,440. Further background information is found in the i-STAT® System Manual (Abbott Point of Care, East Windsor, N.J.).

While the present invention is mainly described for systems where the physiological sample is blood, plasma or serum, including reagent-amended and diluted forms, it is also applicable to the analysis of other biological materials such as, but not limited to, urine, saliva, vaginal, fecal, bronchial and gastric secretions. The disposable diagnostic devices can include, for example, urine analysis devices, saliva analysis devices, and cheek swab analysis devices.

In the present application, the terms "blood" and "whole blood" are used interchangeably and refer to freshly drawn blood which may be drawn into a vacutainer, and which may contain an anticoagulant, or to which one or more standard clinical agents may be added in the course of clinical assay.

The blood sample may be taken from arterial, venous or capillary sources from human or animal sources.

The term analyte as used herein refers to a component represented in the name of a measurable quality.

The term "preservative" and "anticoagulant" are used interchangeably herein and refer to prevention of coagulation of cells. Those skilled in the art will understand that many Vacutainer® blood collection tubes may contain lithium and sodium heparin. Other tubes, such as blood collection tubes may contain clot activators such as sodium polyanethol sulfonate.

The use of the singular forms "a", "an", and "the" include pleural references unless the context clearly dictates otherwise.

Unless defined otherwise or the context clearly dictates otherwise, all technical and scientific terms used herein have the same meaning as commonly understood by one of ordinary skill in the art to which this invention belongs.

As indicated above, the exemplary embodiment of the invention are also applicable to other analytical systems known in the art, where a single-use testing device or cartridge has a sensing means. These include ones based on electrochemical principles, e.g. potentiometry, amperometry and conductimetry, and testing systems typically referred to as electrodes, modified electrodes, ion-selective electrodes, enzyme electrodes, immuno-electrodes, strip electrodes, biosensors, immunosensors and the like. These also include ones that are based on optical methods, for example, detecting turbidity, or absorbance at one or more selected wavelength, evanescence, fluorescence, luminescence, wave guides, reflectance and the like. These devices can use similar fluidics to the i-STAT® System, at least to the extent that a test sample is delivered to a testing region in each device, and that the devices are operated with a reading apparatus. Thus the present invention is also applicable to these systems, primarily but not exclusively, where these systems are used at the point of patient care, e.g. the operating room, emergency room and physician's office.

In an exemplary embodiment, the reader is generally handheld, portable or having a small bench-top footprint. It is preferably free-standing, i.e. battery operated, so that it can be easily moved to a bedside location if desired. However, it may be attached to main power or intermittently to a battery recharger attached to main power.

One of the main values of point of care blood testing systems is that the time-consuming need to send a patient's blood sample to a central laboratory for testing is eliminated. These systems are sufficiently easy to operate that a nurse, at the bedside, can obtain a reliable quantitative analytical result, equivalent in quality to the laboratory. In a preferred embodiment, the nurse selects a cartridge with the required panel of tests, draws a blood sample, dispenses it into the cartridge, seals the cartridge and inserts the cartridge into the reading device. The reading device then performs a test cycle, i.e. all the other analytical steps required to successfully generate a test result. Such simplicity gives the physician more speedy insight into a patient's physiological status. In addition, by reducing the time for evaluation, it enables a quicker decision by the physician on the appropriate treatment, thus enhancing the likelihood of a successful patient outcome.

In the emergency room and other acute care locations within a hospital, the types of blood tests required for individual patients tends to vary. Thus, point of care systems generally offer a range of disposable cartridges with different menus of blood tests. In addition to tests for sodium, potassium, chloride, calcium, bicarbonate, partial pressure of oxygen (pO2), partial pressure of carbon dioxide (pCO2), pH, glucose, hematocrit, hemoglobin, ammonium, lactate, blood urea nitrogen (BUN) and creatinine, others can include prothrombin time (PT), PT/international normalized ratio (INR), activated clotting time (ACT), activated partial thromboplastin time (APTT), hemoglobin AlC, heparin anti-Xa, blood culture, troponin I, troponin T, creatine kinase MB (CKMB), brain natriuretic peptide (BNP), NTproBNP and C-reactive protein (CRP). As is well known in the art, several other parameters can be calculated from these test results, including for example base excess (BE), anion gap, and percentage of oxygen saturation (% O2 sat). These tests can be provided in several combinations presented to the user is a single-use device, e.g. disposable cartridge. For example, the i-STAT® system offers hospitals more than ten types of cartridges with menus that range from one to eight or more blood tests. These test menus are configured so that each test is compatible with a given anticoagulant, and the manufacture specifies the given anticoagulant or anticoagulant options in the product literature. Where tests require different anticoagulants, they are provided in separate cartridges, and the product literature indicates the appropriate anticoagulant for each. For example, the 3.2% citrate concentration is preferred for coagulation testing.

As a result, a given user, e.g. a hospital, may use multiple types of cartridges and need to ensure the quality of test results, e.g. the correct sample collection protocol, at each point of care testing location. These locations can include, for example an emergency room (ER), critical care unit (CCU), pediatric intensive care unit (PICU), intensive care unit (ICU), renal dialysis unit (RDU), operating room (OR), cardiovascular operating room (CVOR) and general wards (GW). Alternatively, the user may be a physician's office, clinic, laboratory, ambulance or visiting nurse service. However the need to ensure quality is the same.

In one example of the present invention, it is necessary to consider the situation where a collection tube with the anticoagulant $K_3EDTA$ (tri-potassium ethylenediamine tetraacetic acid), is incorrectly used to run an EG7+ cartridge on the i-STAT system. The EG7+ cartridge has the following menu of tests; K, Na, iCa, pH, $pCO_2$, $pO_2$ and hematocrit, and all tests are based on electrochemical sensing principles. Note that the same considerations discussed here for the EG7+ cartridge also apply to the i-STAT® CG8+ cartridge which has the following menu; hematocrit, Na, K, ionized calcium (iCa), pH, pCO2, $pO_2$ and glucose; the i-STAT® CHEM8+ cartridge with a menu of: hematocrit, Na, K, iCa, Cl, $TCO_2$ (total carbon dioxide), creatinine, BUN, glucose, and the i-STAT® EG+ cartridge which has the following menu, K, Na, Cl, BUN, glucose and hematocrit. In addition, the same considerations apply whether the tube contains $K_3EDTA$ or $K_2EDTA$. $K_3EDTA$ is a liquid and will dilute the sample about 1-2% whereas $K_2EDTA$ is spray-dried on the walls of the tube and will not dilute the sample. The latter (with two potassium ions per EDTA) is now generally the preferred EDTA salt for anticoagulation in clinical analyses.

In accordance with exemplary embodiments, $K_3EDTA$ is the anticoagulant. The presence of the $K_3EDTA$ has several effects on the blood sample. The potassium that is naturally present in the sample is now augmented by that associated with the EDTA. As the potassium ion sensor in the cartridge is obviously unable to distinguish the two different sources of potassium, this give an inaccurately elevated test value for the patient sample. Note that a normal patient potassium value is about 4 mM, whereas the presence of the added potassium associated with the EDTA results in the measured value being generally above about 9 mM. Note that this value is an abnormal value, well above one that is likely to be seen physiologically in human samples. In the prior art i-STAT® system's mode of operation, this value would be flagged on the reader display, as it is out of the reportable range, and may also be indicative of other types of system error, e.g. a potassium sensor that is not performing to specification, or a sample compromised by hemolysis. Table 1 shows the reportable range for analytes tested by the i-STAT® system.

TABLE 1

| Analyte | Unit | Reportable Range |
|---|---|---|
| Hematocrit (Hct) | % Packed Cell Volume (PCV) | 10-75 |
| Na | mmol/L | 100-180 |
| K | mmol/L | 2.0-9.0 |

TABLE 1-continued

| Analyte | Unit | Reportable Range |
|---|---|---|
| iCa | mmol/L | 0.25-2.50 |
| Cl | mmol/L | 65-140 |
| BUN | mg/dL | 3-140 |
| Glucose | mg/dL | 20-700 |
| Creatinine | mg/dL | 0.2-20 |
| $TCO_2$ | mmol/L | 5-50 |
| $pCO_2$ | mmHg | 5-130 |
| $pO_2$ | mmHg | 5-800 |
| pH | $-\log[H^+]$ | 6.5-8.2 |
| ACT-celite | seconds | 50-1000 |
| ACT-kaolin | seconds | 50-1000 |
| PT-INR | ratio | 0.9-8.0 |
| Cardiac troponin-I | ng/mL | 0.00-50.00 |
| Creatinine Kinase MB | ng/mL | 0.0-150.0 |
| BNP | pg/mL | 15-5000 |

Another effect of $K_3EDTA$ on the blood sample is for the EDTA to bind essentially all of the divalent metal ions in the blood sample, notably the ionized calcium and magnesium. As a result, the measured calcium value for the sample will be less than 0.1 mM, or essentially zero. Again, this is a value that is non-physiological and out of the reportable range (see Table 1). This result would have been suppressed or flagged on the prior art i-STAT® system. The same type of reasoning for potassium, mentioned above applies, as the cause of the flagged result cannot necessarily be ascribed to the wrong anticoagulant but could also be an inherent sensor or system error, or other pre-analytical error such as hemolysis.

Example 1

Table 2 shows data for i-STAT CHEM8+ test cartridge, including calculated values, using EDTA, lithium heparin and no anticoagulant, and the allowable total error (ATE) for each test. ATE values at the normal and clinical decision points are shown.

Example 2

The observation that led to the present invention, arose when the same sample as above, was collected and tested in the correct collection tubes, i.e. one with either no anticoagulant or one with lithium heparin (LiHep), and also the incorrect collection tubes containing $K_2EDTA$, $K_3EDTA$, $Na_2EDTA$, trisodium citrate and a mixture of potassium oxalate and sodium fluoride, as shown in Table 2. Surprising results were recorded in Table 2 for some of the other tests that comprise the CHEM8+ test cartridge menus. These results are shown in Table 2 with the ATE and ½ATE for each test.

TABLE 2

| Collection Tube ATE: | Analyte | | | | | | | | |
|---|---|---|---|---|---|---|---|---|---|
| | Hct, % PCV | Na, mmol/L | K, mmol/L | iCa, mmol/L | Cl, mmol/L | BUN, mg/dL | glucose, mg/dL | creatinine, mg/dL | TCO2, mmol/L |
| | 4.7 | 4.0 | 0.5 | 0.05 | 5.2 | 2.0 | 10.2 | 0.3 | 4.0 |
| Lithium heparin (control) | 44.2 | 141.1 | 3.80 | 1.244 | 104.6 | 12.0 | 101.8 | 0.83 | 26.9 |
| Bias (observed-control no anticoagulant | 0.1 | 0.7 | 0.16 | 0.018 | -0.1 | 0.1 | 3.2 | 0.06 | -1.1 |
| $K_2EDTA$ | -2.8 | -14.1 | 17.2 | -1.24 | 9.9 | 1.5 | 0.0 | 0.05 | -0.7 |
| $K_3EDTA$ | -4.5 | -17.0 | 22.0 | -1.24 | 13.8 | 2.2 | -1.2 | 0.04 | 0.4 |
| $Na_2ETDA$ | 0.0 | 5.8 | -0.17 | -1.24 | -0.9 | -0.1 | 0.5 | 0.05 | -1.1 |
| potassium oxalate/NaF | -13.1 | 44.5 | 24.4 | -1.23 | 10.1 | -0.7 | -6.4 | -0.11 | 2.1 |
| trisodium citrate | -6.1 | -2.0 | -0.81 | -1.19 | 3.2 | -2.8 | -12.1 | -0.01 | -4.1 |

▨ = indicates bias larger than 1/2 Allowable Total Error (ATE).

Note that ATE limits for analytes are generally derived from the Clinical Laboratory Improvement Act (CLIA). As a guideline for accuracy, a result that is biased from the true result by less than the ATE value is associated with an acceptable risk to patient safety. Commercial systems, e.g. the i-STAT® system, generally apply a tighter criterion of ½ATE to study protocols. Table 2 shows ATE values at the normal and clinical decision points. Note that the tests where there is a bias larger than ½ATE are indicated by shaded boxes.

Figure 2:
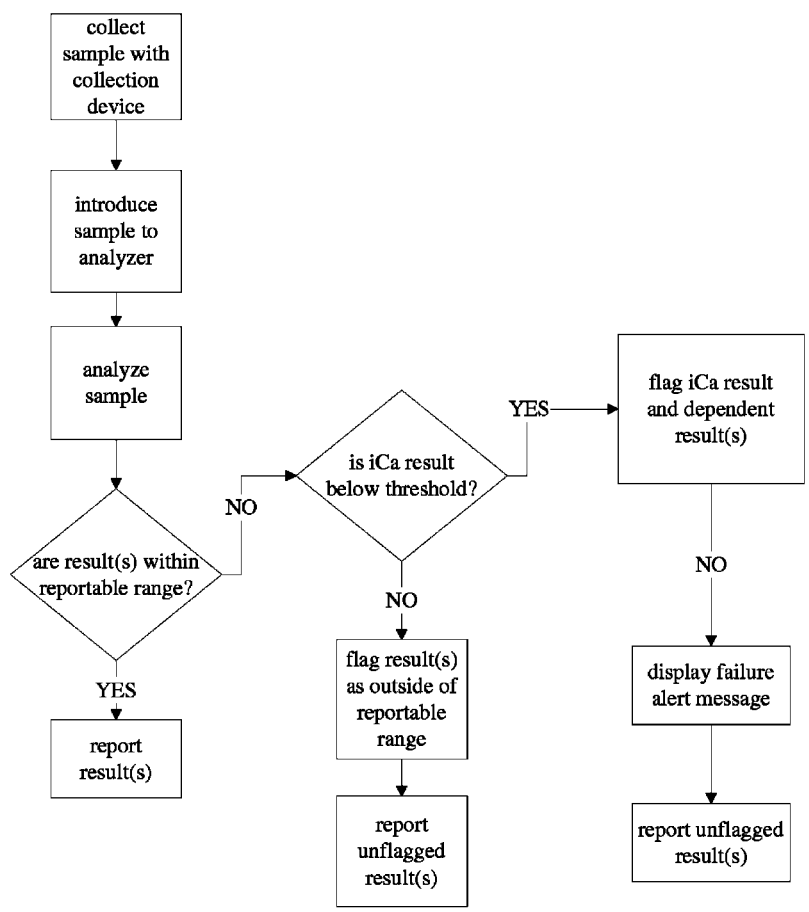
FIG. 2 is a flow chart illustrating a new algorithm capable of flagging tests that exhibit an undesirable allowable total error (ATE) where the sample was incorrectly collected using EDTA, in accordance with exemplary embodiments of the present invention.
Figure 3:
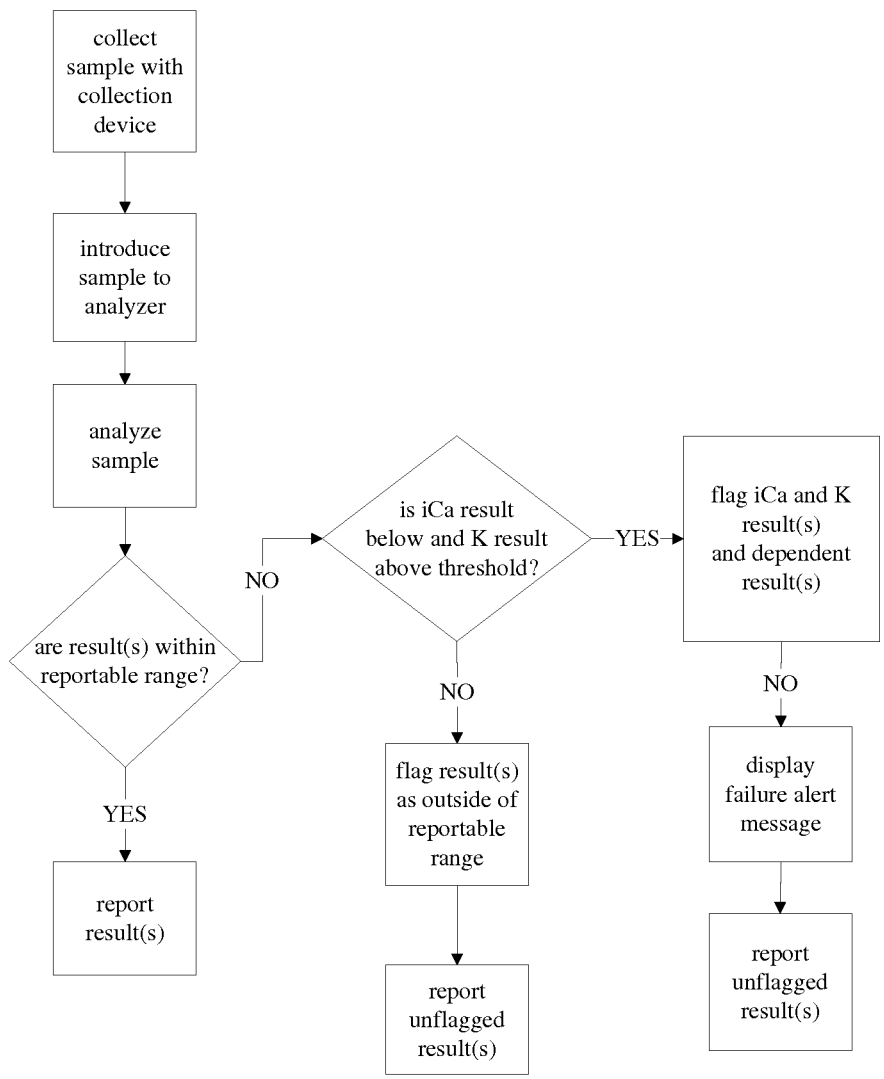
FIG. 3 is a flow diagram of a new algorithm capable of flagging tests that exhibit an undesirable ATE where the sample was incorrectly collected using EDTA, in accordance with exemplary embodiments of the present invention.

With regard to EDTA salts, a composite view of the tests of CHEM8+ test cartridge in Table 2, indicates that only glucose, $TCO_2$ and creatinine results are completely unaffected. Slightly lower values were observed for Na, pH and hematocrit in the presence of EDTA salts, and partially elevated values were observed for $pO_2$, $pCO_2$, BUN and chloride. Importantly, all these values were still well within the normal expected range of values. As a result, it is necessary to determine whether the difference places a given test outside the ATE as described above. With regard to the algorithms discussed here, the typical prior art version is shown in FIG. 1. FIG. 1 shows the prior art algorithm for flagging erroneous test results where only the directly affected test is flagged. While the prior art i-STAT® system would not have previously suppressed any of these results, the new algorithm shown in FIG. 2 and FIG. 3, is capable of suppressing results for those tests where the incorrect use of EDTA will cause tests to have an unacceptable ATE.

Note that Table 2 also shows that with the anticoagulants trisodium citrate and a mixture of potassium oxalate and sodium fluoride, only creatinine is substantially unaffected based on the ½ATE criterion. Likewise the new algorithms in FIG. 2 and FIG. 3 can be applied to these anticoagulants.

Example 3

Table 3 shows data for i-STAT® CG8+ test cartridges, including calculated values, using $K_2EDTA$ and lithium heparin, and the allowable total error (ATE) for each test. ATE values at the normal and clinical decision points are shown.

TABLE 3

| Collection Tube ATE: | Analyte | | | | | | | |
|---|---|---|---|---|---|---|---|---|
| | Hct, % PCV | Na, mmol/L | K, mmol/L | iCa, mmol/L | glucose, mg/dL | pH | pCO$_2$ | pO$_2$ |
| | 4.7 | 4.0 | 0.5 | 0.05 | 9.5 | 0.04 | 5.0 | 5.0 |
| Lithium heparin (control) | 43.7 | 139.2 | 3.86 | 1.143 | 95.7 | 7.391 | 44.7 | 28.8 |
| K$_2$EDTA | -2.3 | -14.1 | 16.6 | -1.143 | -1.8 | -0.165 | 18.5 | 16.8 |

▓▓▓ = indicates bias larger than 1/2 Allowable Total Error (ATE).

Note that only glucose and hematocrit are unaffected by EDTA and the algorithms in FIGS. 2 and 3 can be used to automatically suppress results for Na, K, iCa, pH, pCO2 and pO2.

Example 4

Table 4 shows data for i-STAT EG7+ test cartridges, including calculated values, using $K_2EDTA$ and lithium heparin, and the allowable total error (ATE) for each test. ATE values at the normal and clinical decision points are shown.

TABLE 4

| Collection Tube ATE: | Analyte | | | | | | |
|---|---|---|---|---|---|---|---|
| | Hct, % PCV | Na, mmol/L | K, mmol/L | iCa, mmol/L | pH | pCO$_2$ | pO$_2$ |
| | 4.7 | 4.0 | 0.5 | 0.05 | 0.04 | 5.0 | 5.0 |
| Lithium heparin (control) | 38.7 | 137.2 | 4.17 | 1.236 | 7.339 | 51.1 | 21.9 |
| K$_3$EDTA | -4.0 | -19.6 | -22.3 | -1.236 | -0.127 | 4.0 | 24.5 |

▓▓▓ = indicates bias larger than 1/2 Allowable Total Error (ATE).

Note that none of the tests are unaffected by EDTA and the algorithms in FIGS. 2 and 3 can be used to automatically suppress all results. It is noted that data for K$_3$EDTA with EG7+ shows a greater impact on hematocrit (HCT) than does K$_2$EDTA with CG8+. This is also the case for the CHEM8+ data in Table 2. The cause for this is two-fold: (a) K3EDTA is a liquid formulation and thus there is a dilution effect, and (b) K$_3$EDTA shrinks the red blood cells more than does K$_2$EDTA. This is well known in the art, and is described most authoritatively in Clinical Laboratory Standards Institute H7-3A (Wayne, Pa.).

According to exemplary embodiments, to avoid the risk of reporting incorrect results with an EG7+ test cartridge run with an EDTA sample, the new method provides an algorithm that performs the following functional steps; if the measured potassium is above a threshold value, e.g. 9 mM, and the measured ionized calcium value is below a threshold, e.g. 0.2 mM, then no result is displayed for the cartridge tests, along with a message that the sample was incorrectly collected in a tube with the wrong anticoagulant, e.g. EDTA. FIG. 3 shows this new algorithm in schematic form. It is capable of flagging tests that exhibit an undesirable ATE where the sample was incorrectly collected using EDTA.

Note that where a magnesium ion (Mg) test is also part of the menu, this test will also be affected by EDTA. As a result, it can be used as part of the algorithm, where a Mg test value well below the physiological range is used to indicate an incorrect anticoagulation procedure. Typical reference ranges for a reportable magnesium test are: 0.50-0.90 mM for newborns; 0.65-1.05 mM for adults. A suitable threshold value for the disclosed algorithm is 0.2 mM, but can be in the range of about 0.1 mM to about 0.3 mM. Note also that the Mg test can be used in addition to the iCa test or as a substitute. Thus, FIG. 3 can be amended to include boxes with; "is Mg result below and K result above threshold?", or "are iCa and Mg results below and K result above threshold?".

In an exemplary embodiment, it is sufficient that only the calcium value is below a threshold value. Here the algorithm omits the potassium threshold limitation requirement for suppressing results. FIG. 2 shows this new algorithm which is capable of flagging tests that exhibit an undesirable ATE where the sample was incorrectly collected using EDTA. A limitation of this second embodiment is the requirement that the calcium sensor be able to clearly distinguish that it is genuinely measuring a non-physiological calcium value, rather than just being a sensor that is not performing to specification. If it is the latter, only the calcium test value would need to be suppressed and the others can reliably be reported. An advantage of the algorithm shown in FIG. 3 is that it has greater robustness.

With regard to the actual method of reporting the erroneous use of EDTA to the user, this can be by means including a flagged display, suppressed result, a printed message, an alert screen and an alert sound or message. Other similar methods will be apparent to those skilled in the art.

In another exemplary embodiment of the utility of the present invention, there is the likelihood that a user of the i-STAT® system will want to run a BNP test cartridge at the same time as a CHEM8+. Both these cartridges are useful in assessing patients suspected of congestive heart failure. The BNP test cartridge requires K$_2$EDTA as a preservative, whereas CHEM8+ uses either lithium heparin or no anticoagulant. As a result, the user must collect sample in the correct tubes and match the tubes and cartridges correctly. As the CHEM8+ cartridge has tests for Na, K, Cl, iCa, TCO2, glucose, urea, creatinine and hematocrit, if a K$_2$EDTA is incorrectly used for sample collection, the new algorithms shown in FIGS. 2 and 3 will recognize it and flag or suppress all affected results, including the calculated anion gap parameter.

In an exemplary embodiment, the invention accounts for the possibility of using the present method to alert another test system which is performing a test using the same sample or a sample collected in the same way. It is not uncommon for a sample to be tested at a point of care location and then the sample transported to a central laboratory for further testing. For example, where the algorithm disclosed above has determined that a particular sample was incorrectly collected with the wrong anticoagulant, the instrument can send a message from a point of care location to a central laboratory, alerting the laboratory that an identified sample was corrected incorrectly. Note that sample collection tubes are typically bar coded at the point of collection to identify the patient (and record other information), thus the laboratory has identification means (a barcode reader) for matching a tube that arrives in the laboratory with a specific alert or message. Those skilled in the art will recognize that instruments used for blood analysis at the point of care are often linked to a hospital's laboratory information system (LIS) enabling data management and billing. Such connectivity can be provided by traditional wired means, or wirelessly using well known protocols. Other means for transmission of information of this kind to another location, will be apparent to those skilled in the art of data management.

Regarding the terms flagged and suppressed with reference to reported results. The algorithm and instrument software can for example flag a particular test result, i.e. report it as a usable result, but flag or in another similar way identify it as a result that was not obtained under ideal conditions. Based on the discussion of ATE, it will be apparent to those skilled in the art that while an incorrect sampling method may have been use, some of the test results are substantially unaffected and can still be used, or are marginally affected and can be used with caution. With respect to the term suppression, this means that the instrument does not display a specific test concentration value, but substitutes an asterisk or some other similar symbol to indicate that no result is being reported.

In another exemplary embodiment of the utility of the present invention summarized in Table 2, a CHEM8+ cartridge is used erroneously with other different anticoagulants. Data in this table show results for cartridges run with potassium oxalate/sodium fluoride and trisodium citrate collection tubes. Note that the potassium oxalate/sodium fluoride combined preservative has the effect of increasing sodium by about 45 mM, potassium by about 24 mM and reducing calcium to about 0.015 mM. The effect on the other tests on the CHEM8+ menu will be flagged by the algorithm shown in FIG. 3. Note that in this context FIG. 3 can be amended to include boxes with; "is iCa result below and Na result above threshold?", or "is iCa results below and K and Na result above threshold?".

With regard to threshold values in the algorithms the following are preferred; where the cation is sodium and the threshold is above about 160 mM; where the cation is potassium and the threshold is above about 9 mM; where the calcium threshold is about 0.25 mM; and where the cation is magnesium the threshold value is about 0.2 mM. Those skilled in the are will recognize that the calcium threshold is best selected in the range of about 0.3 mM to about 0.001 mM, and that the potassium threshold is best selected in the range of about 8 mM to about 20 mM.

Regarding the applicability of the inventions to other tests beyond those mentioned above, one skilled in the art will recognize that, based on the teaching presented here, no undue experimentation is needed. A new test can be assessed for the affect of an incorrect anticoagulation procedure on the ATE, as described above. If the affect is less than ½ATE then there is no need to flag the test when the disclosed algorithms are used. However, if the affect is greater than ½ATE then the test can be flagged or suppressed. By way of example, the method is applicable to tests including lactate, lithium, bilirubin and cholesterol.

In an exemplary embodiment, the divalent cation is calcium or magnesium and the monovalent ion is potassium or sodium. Here, the other analyte species are typically picked from among calcium, magnesium, potassium sodium, hydrogen, chloride, bicarbonate, ammonium, lithium, pH, pCO2, pO2, glucose, creatinine, lactate, blood urea nitrogen, and hematocrit. Where the divalent cation is calcium, the threshold is about preferably about 0.25 mM and can be a selected value in the range of about 0.3 mM to about 0.001 mM. Where the monovalent ion is potassium, the threshold is preferably about 9 mM and typically a selected value in the range of about 8 mM to about 20 mM. Where the divalent cation is magnesium and the threshold is preferably about 0.2 mM and where the monovalent ion is sodium and the threshold is preferably about 160 mM.

As discussed above, in an alternative embodiment the algorithm can include a second divalent cation concentration determination, which causes flagging or suppression of results, but requires both the first and second divalent cation concentrations to surpass a preselected threshold value for each. Another related embodiment has a method where a second monovalent ion concentration is determined. Here, flagging or suppression of results requires both first and second monovalent ion concentrations to surpass a preselected threshold value for each.

In an exemplary embodiment, the determination of the monovalent ions, the divalent cations and all the other analyte species concentrations are determined electrochemically. Notably, the determination of the divalent cation concentration is performed by a calcium ion-selective electrode or magnesium ion-selective electrode, and determination of the monovalent ion concentration is performed by a potassium ion-selective electrode or sodium ion-selective electrode.

In another exemplary embodiment, the other analyte species concentrations are determined by potentiometric sensors, amperometric sensors and conductimetric sensors. However, sensors based on optodes, flame photometry, ion-sensitive dyes, an ion-dependent enzyme assays and enzyme assays can be used.

In other exemplary embodiments, the determination of the divalent cation concentration can be by a sensor selected from the group; ion-selective electrode, potentiometric sensor, optode, flame photometer, ion-sensitive dye and divalent cation-dependent enzyme assay. Likewise the determination of the monovalent ion concentration can be by a sensor selected from the group; ion-selective electrode, potentiometric sensor, optode, flame photometer, ion-sensitive dye and ion-dependent enzyme assay.

In one embodiment, the present invention is embodied within an analyzer instrument, e.g. a laboratory analyzer, with one or more reusable sensors, including a sensor for a divalent cation, a sensor for a monovalent ion and at least one other analyte species sensor. However, in the preferred embodiment the analyzer instrument comprises an analyzer used in combination with a single-use test cartridge having one or more sensors including a sensor for a divalent cation, a sensor for a monovalent ion and at least one other analyte species sensor. Note that in both cases test results are reported by means of a displayed message on the screen of the analyzer, a printed message or an audio message.

Regarding sample collection, in a typical embodiment the collection device is a tube with a stopper sealing the entry to the tube and where the interior of the tube is under a partial vacuum. Alternatively, the collection device is an open collection tube, evacuated tube, syringe or capillary tube. Here, the sample will generally be blood, plasma or serum. Note that the sample may be diluted with water or buffer, or be amended by adding reagent, e.g. enzyme, dyes, antibodies, enzyme cofactors and substrates and the like.

While the invention is generally anticipated to be performed at a location such as an emergency department, operating room, physician's office or ambulance, other suitable point-of-care locations will be apparent to those skilled in the art.

As mentioned above, those skilled in the art will recognize that suppressing or flagging a measured value of an analyte, e.g. an ionic species, based on it alone exceeding a threshold value is widely used. However, the present method discloses means for systematically identifying other measured species, that alone do not exceed a threshold, but which should be suppressed or flagged. In addition, the present method provides automatic means for identifying blood samples that were collected with the wrong anticoagulation protocol, for a given test or set of tests. As a result, the present method provides a useful advance in the clinical chemistry arts for providing quality results on patient samples.

The above description provides examples in accordance with the present invention. However, while the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

All United States patents and patent applications, foreign patents and patent applications, and publications discussed above are hereby incorporated by reference herein in their entireties to the same extent as if each individual patent, patent application, or publication was specifically and individually indicated to be incorporated by reference in its entirety.

What is claimed is:

1. A method of identifying erroneous collection of a sample for a measurement of a first species in a collection device comprising a reagent incompatible with a reliable measurement of said first species, said method comprising:
   taking the sample from said collection device;
   determining a concentration of said first species;
   determining a concentration of a second species in said sample with respect to a threshold value;
   when the concentration of the second species is beyond said threshold value, flagging or suppressing a reporting of the determined concentration of said first species and the determined concentration of said second species, and reporting the collection device as being inappropriate for collection of said sample for the reliable measurement of said first species; and
   when the concentration of the second species is not beyond said threshold value, flagging or suppressing the determined concentration of the first species if the determined concentration of the first species is outside of a reportable range for the first species, flagging or suppressing the determined concentration of the second species if the determined concentration of the second species is outside of a reportable range for the second species, and not reporting the collection device as being inappropriate for collection of said sample for the reliable measurement of said first species,
   wherein said first species is one of a plurality of species in said sample.

2. An automatic method for determining that a sample was collected with a wrong anticoagulant, the method comprising:
   (a) adding the sample to an analyzer instrument having means for analyzing analyte species within the sample that include a divalent cation and one or more other analytes,
   (b) determining a concentration of the divalent cation and a concentration of the one or more other analytes in said sample,
   (c) comparing the determined concentration of the divalent cation to a predetermined lower threshold value,
   (d) when said predetermined lower threshold value is surpassed by the determined concentration of the divalent cation, said analyzer instrument flags or suppresses the determined concentration of the divalent cation and the determined concentration of the one or more other analytes in said sample, and reports that the sample was collected with the wrong anticoagulant, and
   (e) when said predetermined lower threshold value is not surpassed by the determined concentration of the divalent cation, said analyzer instrument does not flag or suppress the determined concentration of the divalent cation and the determined concentration of the one or more other analytes if the determined concentration of the one or more other analytes is not outside of a reportable range for the one or more other analytes, and said analyzer instrument does not report that the sample was collected with the wrong anticoagulant.

3. The method of claim 2, wherein the divalent cation is calcium.

4. The method of claim 2, wherein said one or more other analytes is selected from the group consisting of: magnesium, potassium sodium, hydrogen, chloride, bicarbonate, ammonium, lithium, pH, partial pressure of carbon dioxide ($pCO_2$), partial pressure of oxygen ($pO_2$), glucose, creatinine, lactate, blood urea nitrogen, and hematocrit.

5. The method of claim 2, wherein the divalent cation is calcium and the predetermined lower threshold value is a selected value in the range of about 0.3 mM to about 0.001 mM.

6. The method of claim 2, wherein the wrong anticoagulant is selected from the group consisting of: $K_2EDTA$, $K_3EDTA$, and $Na_2EDTA$, oxalic acid and salts thereof, ethylene glycol tetra acetic acid (EGTA) and salts thereof, citric acid and salts thereof, fluorides, non-balanced heparins, and combinations thereof.

7. A method of identifying erroneous collection of a sample for a measurement of a first species in a collection device comprising a reagent incompatible with a reliable measurement of said first species, said method comprising:
   taking the sample from said collection device;
   determining a concentration of said first species;
   determining a concentration of a second species in said sample with respect to a threshold value;
   when the concentration of the second species is beyond said threshold value, flagging or suppressing a reporting of the determined concentration of said first species and the determined concentration of said second species, and reporting the collection device as being inappropriate for collection of said sample for the reliable measurement of said first species; and
   when the concentration of the second species is not beyond said threshold value, flagging or suppressing the determined concentration of the first species if the determined concentration of the first species is outside of a reportable range for the first species, flagging or suppressing the determined concentration of the second species if the determined concentration of the second species is outside of a reportable range for the second species, and not reporting the collection device as being determined to be inappropriate for collection of said sample for the reliable measurement of said first species,
   wherein said second species is one of a plurality of species.

8. A method of identifying erroneous collection of a sample for a measurement of at least one species in a collection device containing a reagent incompatible with a reliable measurement of said at least one species, the method comprising:
   taking the sample from said collection device;
   determining a concentration of said at least one species;
   determining a concentration of a plurality of other species in the sample with respect to a threshold value;
   when the concentration of the plurality of other species is beyond said threshold value, flagging or suppressing a reporting of the determined concentration of said plurality of other species and the determined concentration said at least one species, and reporting the collection device as being inappropriate for collection of said sample for the reliable measurement of said at least one species; and
   when the concentration of the plurality of other species is not beyond said threshold value, flagging or suppressing the determined concentration of the at least one species if the determined concentration of the at least one species is outside of a reportable range for the at least one species, flagging or suppressing the determined concentration of the plurality of other species if the determined concentration of the plurality of other species is outside of a reportable range for the plurality of other species, and not reporting the collection device as being inappropriate for collection of said sample for the reliable measurement of said at least one species.

9. An automatic method for determining that a collection device was incorrectly used to collect a bleed sample for analysis of ionic species, the method comprising:
   adding the sample from the collection device to an analyzer instrument having means for analyzing said ionic species that include a divalent cation and one or more other ionic species;
   determining a concentration of the divalent cation and a concentration the one or more other ionic species in said sample;

comparing the concentration of the divalent cation to a predetermined threshold value;

when said predetermined threshold value is surpassed by the determined concentration of the divalent cation, said analyzer instrument flags or suppresses the determined concentration of the divalent cation and the determined concentration of the one or more other ionic species in said sample, and said analyzer instrument reports that the sample was incorrectly collected using the collection device; and when said predetermined lower threshold value is not surpassed by the determined concentration of the divalent cation, said analyzer instrument flags or suppresses the determined concentration of the divalent cation if the determined concentration of the divalent cation is outside of a reportable range for the divalent cation, said analyzer instrument flags or suppresses the determined concentration of the one or more other ionic species if the determined concentration of the one or more other ionic species is outside of a reportable range for the one or more other ionic species, and said analyzer instrument does not report that the sample was incorrectly collected using the collection device.

10. The method of claim 9, wherein the collection device comprises EDTA.

11. An automatic analyte testing method for distinguishing samples incorrectly collected with a wrong anticoagulant from samples collected using a correct anticoagulant, the method comprising:

(a) introducing a sample into an analyzer instrument having means for determining a concentration of a first analyte and a concentration of a second analyte in said sample;

(b) comparing the concentration of the first analyte concentration to a predetermined threshold concentration value;

(c) when the predetermined threshold concentration value is not surpassed by the concentration of the first analyte, reporting by said analyzer instrument the concentration of the first analyte and the concentration of the second analyte, and not reporting by said analyzer instrument that the sample was incorrectly collected with the wrong anticoagulant, and (d) when the predetermined threshold concentration value is surpassed by the concentration of the first analyte, reporting by said analyzer instrument that the concentration of the first analyte and the concentration of the second analyte should not be used, and reporting by said analyzer instrument that the sample was incorrectly collected with the wrong anticoagulant.

* * * * *